United States Patent [19]

Evans et al.

[11] Patent Number: 5,679,517

[45] Date of Patent: Oct. 21, 1997

[54] ANALYTICAL METHODS AND PROBES FOR THE IDENTIFICATION OF CHROMOSOMAL ABERRATIONS AND THE DIAGNOSIS OF GENETICALLY-BASED DISEASE STATES

[75] Inventors: Glen A. Evans, Encinitas; Licia Selleri, Del Mar; Gary G. Hermanson, Encinitas, all of Calif.

[73] Assignee: The Salk Institute For Biological Studies, La Jolla, Calif.

[21] Appl. No.: 324,899

[22] Filed: Oct. 18, 1994

Related U.S. Application Data

[63] Continuation of Ser. No. 673,057, Mar. 20, 1991.
[51] Int. Cl.$^6$ .............................. C12Q 1/68; C12N 15/01
[52] U.S. Cl. ............................................. 435/6; 435/172.3
[58] Field of Search ......................................... 435/6, 172.3

[56] References Cited

PUBLICATIONS

Griffin et al. (1986), Proc. Natl. Acad. Sci. USA 83 : 6122–6126.

*Primary Examiner*—Mindy Fleisher
*Assistant Examiner*—Nancy J. Degen
*Attorney, Agent, or Firm*—Gray Cary Ware & Freidenrich; Stephen E. Reiter

[57] ABSTRACT

Methods for identifying the existence, and optionally the location, of chromosomal aberration(s) in the genome of an organism are disclosed. Intact, chromosomal DNA is hybridized with one or more clones constructed from chromosomal DNA derived from an organism of the same species as the organism to be tested. By identifying the existence of a chromosomal aberration, the susceptibility of an individual to certain disease states can be predicted, and/or the nature of a given disease state can be ascertained with greater certainty.

9 Claims, 3 Drawing Sheets

ANALYTICAL METHODS AND PROBES FOR THE IDENTIFICATION OF CHROMOSOMAL ABERRATIONS AND THE DIAGNOSIS OF GENETICALLY-BASED DISEASE STATES

This application is a continuation application of U.S. Ser. No. 07/673,057, filed Mar. 20, 1991, now pending, the entire contents of which are hereby incorporated by reference herein.

This invention relates to analytical and diagnostic methods. In a particular aspect, this invention relates to methods for identifying the existence of chromosomal aberrations in the genome of an organism. In another aspect, this invention relates to methods for determining the presence and location of chromosomal aberrations in an organism. In yet another aspect, this invention relates to methods for identifying the presence of specific chromosomal aberrations. In a still further aspect, the present invention relates to methods for diagnosing actual or nascent disease states employing the information obtained, applying the invention technique(s) for the determination of the presence and location of chromosomal aberrations.

BACKGROUND OF THE INVENTION

Consistent and specific chromosome translocations have been associated with a number of human malignancies including leukemias, lymphomas and solid tumors. Such translocations may be intimately involved in the molecular pathogenesis of the associated disorders. Accordingly, rapid and effective methods to analyze for the presence of chromosome translocations would be a useful aid in the diagnosis of actual or nascent disease states.

Molecular studies of translocations in solid tumors lag far behind the study of leukemias due to technical difficulties of chromosome analysis in tissue samples. However, by analogy with the translocations associated with chronic myelogenous leukemia and acute lymphoblastic leukemia [t(9;22) (q34;q11); see Hermenes et al., in *Cancer Cells,* 7:21-26 (1989) and Shtivelman et al., in *Nature* 315:550-554 (1985)] and the translocation associated with Burkitt's lymphoma [t(8;22)(q24;q12); see Haluska et al., in *Ann, Rev, Genet.* 21:321-345 (1986)], it is likely that consistent translocations in solid tumors may result in the transposition of two cellular genes giving rise to aberrant expression of a normal gene involved in cellular growth control, or the expression of a chimeric transcriptional unit with distorted physiological function.

Human chromosome 11, for example, is known to contain several sites of chromosome rearrangement associated with tumors, including t(11;22)(q13;q13) rearrangements involving the bcl-1 (breakpoint cluster-1) locus in B cell chronic lymphocytic leukemia, B cell non-Hodgkins' lymphoma, and multiple myeloma; t(4;11)(q21;23) associated with infantile acute lymphoblastic leukemia; and t(9;11) (p22;q23) and t(11;19)9q23;p13) in cases of acute monocytic leukemia.

The t(11;22)(q24;q12) translocations of Ewing's sarcoma (ES), peripheral neuroepithelioma (PNE) and Askin's tumor appear to be cytogenetically identical and represent the presently best described and most consistent chromosome abnormalities associated with solid tumors. Both ES and PNE are small round cell tumors occurring in the trunk or extremities which may arise through transformation of neuroectodermally derived cells. ES cells in culture are reported to express neuroectoderm-associated antigens. Furthermore, ES tumors share a number of histological and immunocytochemical similarities with other tumors derived from neural crest. Moreover, ES and PNE have indistinguishable patterns of expression of various proto-oncogenes and may represent extremes of a spectrum of tumor cell types ranging from more differentiated (PNE) to less differentiated (ES) neuroectodermal cell types.

Molecular analysis of the ES and PNE translocations has in the past been inhibited by the lack of sufficient density of molecular probes to allow precise localization. Molecular analysis has also been inhibited by the lack of cloned genes located near enough to the breakpoint to allow molecular cloning of the site of translocation. Pulsed field gel analysis using a limited number of randomly selected and localized molecular probes has thus far failed to reveal the site of translocation [see Budorf et al., in *Am. J. Human Genetics* 45:128–139 (1989)].

SUMMARY OF THE INVENTION

In accordance with the present invention, we have developed methods useful for determining whether or not chromosome translocations exist. In accordance with the present invention, we have also developed methods useful for determining the presence of a chromosomal translocation, if one exists. Further in accordance with the present invention, we have developed methods useful for differentiating the molecular basis for an observed disease state.

By applying the technique of chromosomal in situ suppression hybridization (CISSH) to ES and PNE metaphase chromosomes using a panel of cosmid markers previously mapped to chromosome 11q [see Lichter et al., *Science* 247: 64–69 (1990)], it has been possible to localize the breakpoint between two closely spaced cosmid clones. Using these clones, high resolution analysis of ES and PNE interphase nuclei allows the localization of the translocation breakpoint on chromosome 11 between the nearest two flanking cosmids to a region of less than 1 mb.

In addition, the gene encoding the leukemia inhibitory factor gene (LIF), known to map to human chromosome 22 in the vicinity of the ES breakpoint, has been found to be translocated to the ES and PNE derivative chromosome 11 to the immediate vicinity of the most centromeric flanking cosmid marker. Since LIF has been shown to suppress in vitro proliferation of myeloid leukemia cell lines and to prevent differentiation of embryonic cells in culture, a chromosome translocation in the vicinity of this gene might be sufficient to induce oncogenesis. However, pulsed field gel analysis demonstrated no abnormalities in a 650 kb region surrounding this locus.

The use of CISSH coupled with panels of landmark cosmid clones has therefore allowed rapid mapping and molecular cloning of the ES and PNE breakpoints. The invention method will also have application as a diagnostic tool for differential diagnosis within the group of mixed round cell tumors where only ES and PNE show this cytogenetic abnormality.

DETAILED DESCRIPTION OF THE INVENTION

Figure 1:
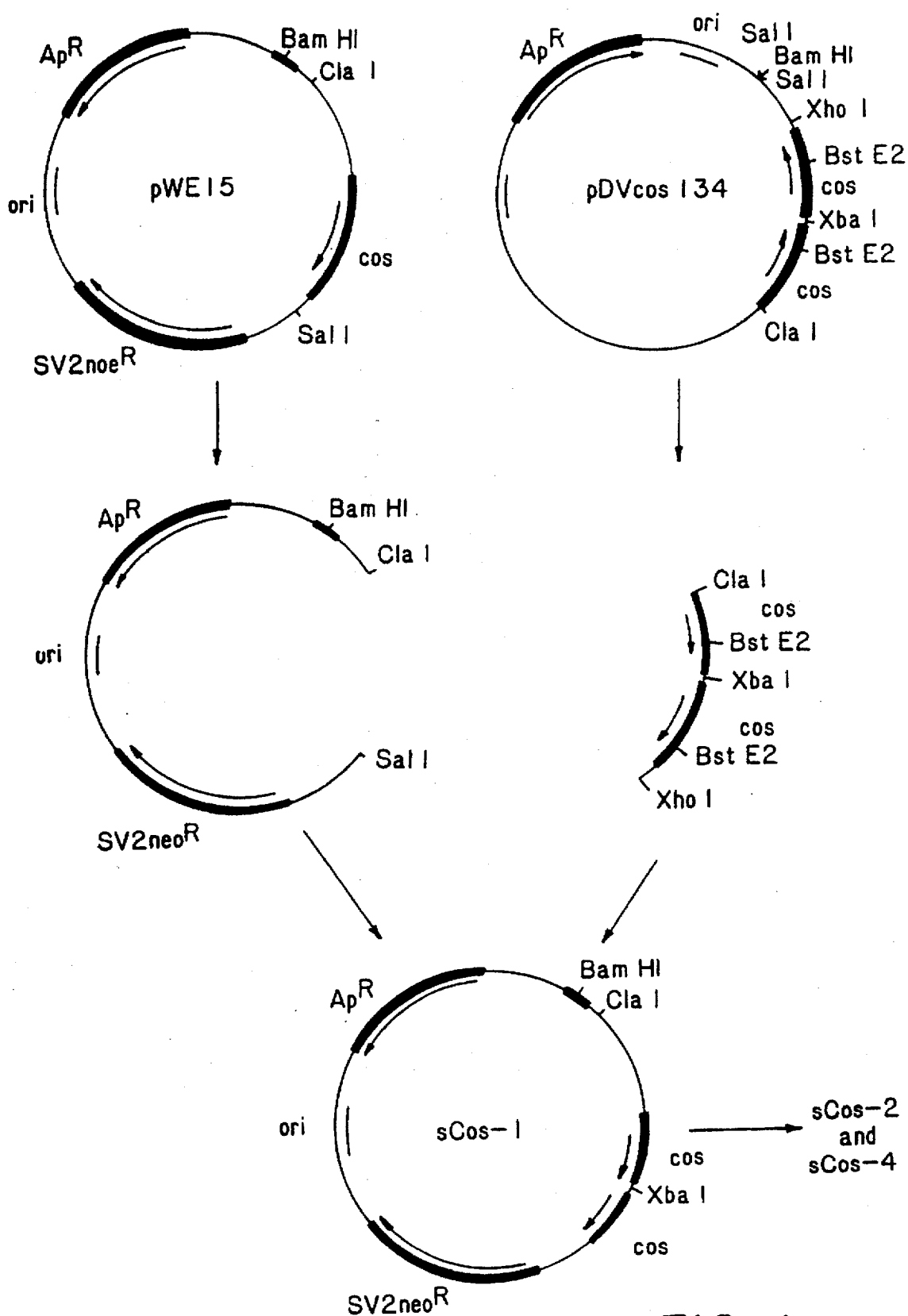
FIG. 1 is a schematic diagram detailing the construction of cosmid cloning vector sCos-1.

In accordance with the present invention, there is provided a method for identifying the existence of chromosomal aberration(s) in the genome of an organism, said method comprising:

(a) hybridizing DNA of intact chromosome(s) from said organism with a panel of clones which recognize total DNA from intact chromosome(s) free of any aberrations, thereby producing a first hybridization pattern, and (b) identifying the existence of chromosomal aberration(s) by comparing said first hybridization pattern with a control hybridization pattern; wherein said control hybridization pattern comprises the pattern obtained when said panel is hybridized with DNA which recognizes intact chromosome(s) free of any aberrations.

In accordance with another embodiment of the present invention, there is provided a method for identifying the presence and location of chromosomal aberration(s) in the genome of an organism, said method comprising:

(a) hybridizing DNA of intact chromosome(s) from said organism with a panel of clones specific for a single aberration-free chromosome which corresponds to the chromosome suspected of containing said aberration(s), thereby producing a first hybridization pattern, and (b) identifying the presence and location of chromosomal aberration(s) by comparing said first hybridization pattern with a control hybridization pattern; wherein said control hybridization pattern comprises the pattern obtained when said panel is hybridized with DNA which recognizes intact chromosome(s) free of any aberrations.

In accordance with yet another embodiment of the present invention, there is provided a method for identifying the presence of a specific chromosomal aberration in the genome of an organism, said method comprising:

(a) hybridizing DNA of intact chromosome(s) from said organism with at least one clone which is diagnostic for the existence of said specific chromosomal aberration, and (b) identifying those organism(s) which give rise to a different hybridization pattern with said clone(s), relative to the hybridization pattern when said clone(s) are hybridized with intact chromosomal DNA free of any aberrations, as containing said specific chromosomal aberration.

In accordance with still another embodiment of the present invention, there is provided a method for determining the presence in a subject of, or susceptibility of a subject to, neuroepithelial tumors associated with chromosome 11,22 translocations, said method comprising:

(a) hybridizing intact chromosomal DNA from said subject with at least one clone specific for chromosome 11 and/or chromosome 22 which is diagnostic for the existence of a chromosome 11,22 translocation, and (b) identifying intact chromosomal DNA which has a different pattern of hybridization, relative to the pattern of hybridization of said panel when hybridized with intact chromosomal DNA free of any aberrations, as being indicative of the presence of, or susceptibility to, neuroepithelial tumors associated with chromosome 11,22 translocations.

Organisms for which the invention technique will find use include, broadly, any vertebrate species, e.g., fowl, fish, reptiles, amphibians, mammals and the like. Presently preferred organisms to be tested employing the invention technique are humans because of the ability to tailor treatment once the cause of an observed disease state is known with some certainty.

The invention technique is capable of identifying the existence of a variety of chromosomal aberrations, e.g., deletions, inversions, duplications, translocations, the formation of ringed chromosomes, and the like.

In accordance with the present invention, a cell sample from the subject organism is contacted with one or more clones constructed from chromosomal DNA derived from an organism of the same species as the organism being tested. The amount of detail provided by a given hybridization reaction is a function of how many clones are used for the hybridization reaction, and how much is known about each probe employed. For example, a single clone could be used, if such clone were diagnostic for a specific aberration of interest, e.g., translocation between chromosome 11 and 22. Such a clone would be derived from that portion of chromosome 11 and/or chromosome 22 where the loss and/or gain of chromosomal DNA occurs upon translocation. Thus, upon hybridization, a different pattern of hybridization between probe and test DNA will be observed, relative to the pattern of hybridization obtained with normal DNA.

Alternatively, a cell sample from an organism suspected of containing a chromosomal aberration can be contacted with a panel of clones, wherein a typical "panel of clones" contains a sufficient number of clones so that, on average, for each chromosome, there are about 300 kilobases between clones. Panels can be a collection of clones which recognize total DNA from intact chromosome(s) free of aberrations, and which are derived from one or more different chromosomes. The hybridization pattern of test sample can then be compared with the hybridization pattern of said panel with normal chromosomal DNA to determine if there are any differences. A different hybridization pattern indicates the existence of one or more aberrations in the test chromosomal DNA.

So long as sufficient information is available about the members of the panel of clones employed, the nature of the specific aberration observed can be determined by correlating the specific differences observed between the control and test hybridization patterns with the particular clone(s) which hybridizes differently in each sample.

Clones employed in the practice of the present invention can be prepared employing a variety of vehicles, such as, for example, cosmids, yeast artificial chromosomes [see, for example, Burke et al., in Science 236: 806–812 (1987)], F1 plasmids [see, for example, O'Connor, et al., in Science 244: 1307–1312 (1989)], P1 bacteriophage [see, for example, Sternberg in Proc. Natl. Acad. Sci. U.S.A. 87: 103–107 (1990)], and the like. Construction of cosmid libraries, for example, has been described by Evans, et al., in Gene 79: 9–20 (1989). For example, cosmid vector sCos-1 has been prepared by digesting pWE15 DNA [described by Evans and Wahl in Methods Enzymol. 152: 604–610 (1987)] with ClaI+SalI and purifying the 6-kb ClaI-SalI fragment lacking the cos sequence (FIG. 1). Cosmid pDVcos134 was digested with ClaI+XhoI, and a fragment containing the duplicated cos region was purified on an LPM agarose gel. The purified fragments were ligated using T4 DNA ligase and transformed into host strain DH5.

Figure 2:
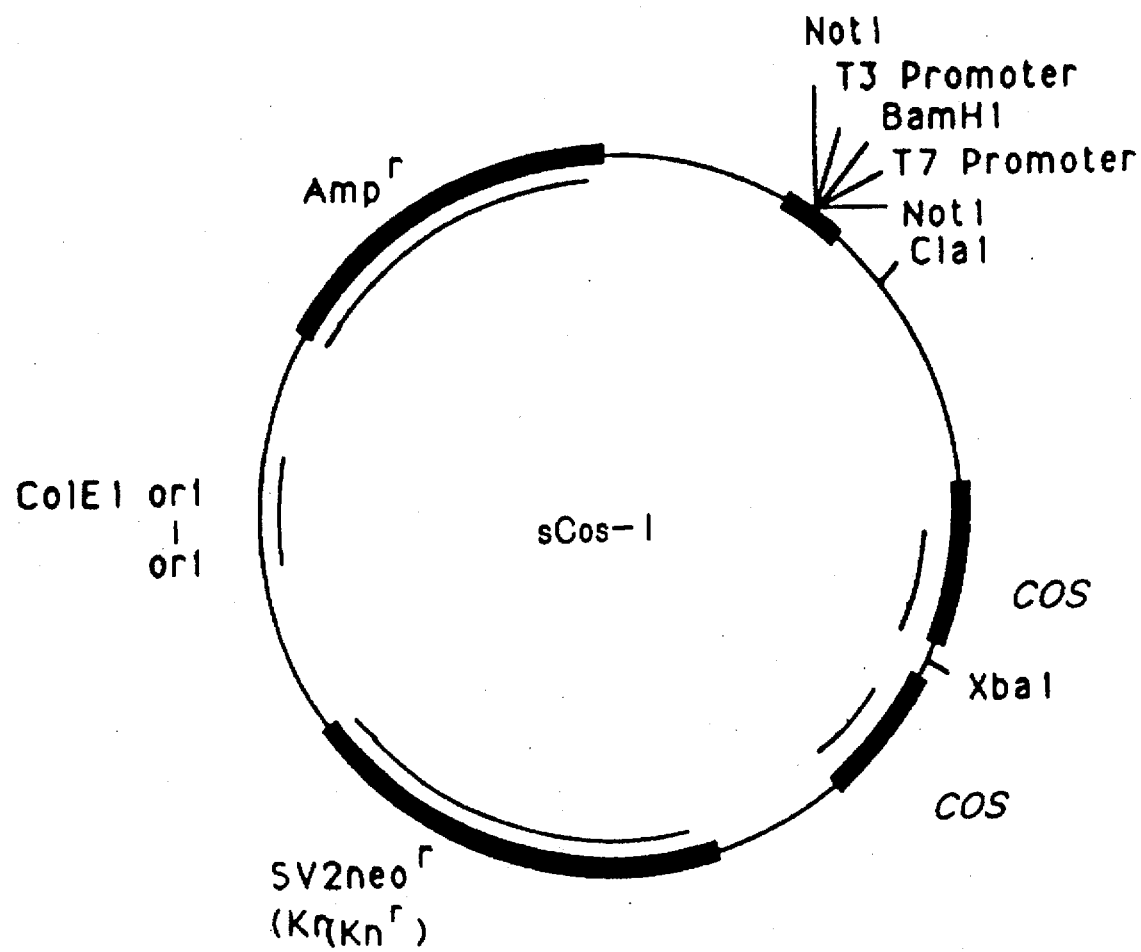
FIG. 2 is detailed restriction map of the cosmid cloning vector sCos-1.

Genomic libraries can be constructed in cosmid vector(s) such as, for example, sCos-1, which contains duplicated cos sites for high efficiency microcloning, T3 and T7 bacteriophage promoters flanking the unique BamHI cloning site, two NotI sites for the excision of genomic inserts, a selectable gene (SV2-neo$^r$) for mammalian gene transfer, and a ColE1 origin of replication (see FIG. 2). Detailed restriction maps of the cosmid insert in this vector may be rapidly determined by an end-labeling mapping procedure using T3- or T7-specific oligonucleotides.

The genomic cosmid library used in this study consisted of 1.5×10$^7$ independent clones and was constructed by using genomic DNA digested to an average size of 100–120 kilobases with MboI, dephosphorylated with calf intestinal phosphatase, ligated with sCos-1 DNA, and packaged with Gigapak Gold (Stratagene) in vitro packaging lysate. Only nonamplified libraries were used, and cosmid clones were archived in 96-well microtiter plates stored at −70° C. in LB media with 15% (vol/vol) glycerol and kanamycin sulfate at 25 μg/ml.

Figure 3:
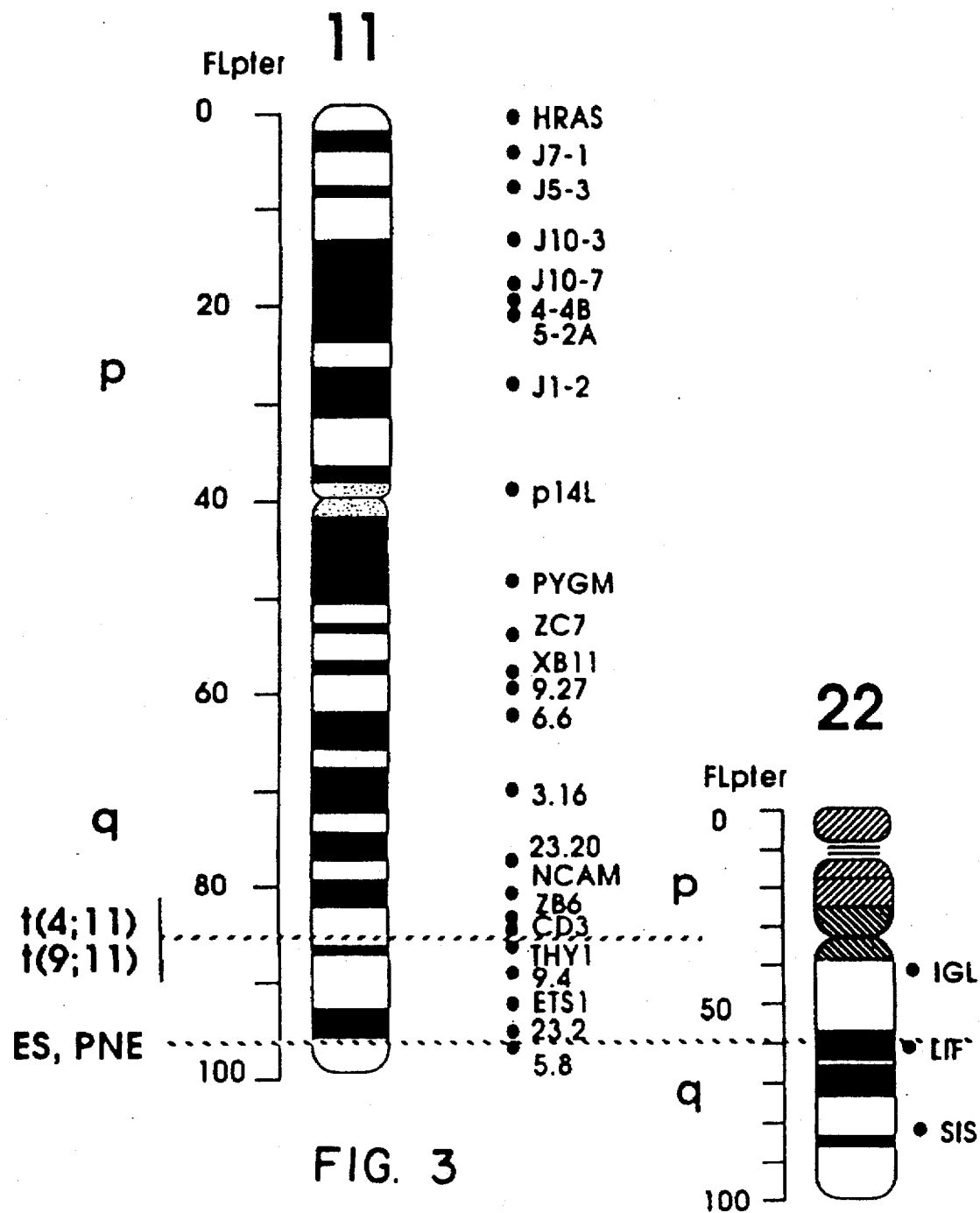
FIG. 3 is a diagrammatic summary of the mapping of numerous probes derived from chromosome 11, with an indication of where the (11,22) translocation occurs in Ewing's sarcoma and peripheral neuroepithelioma.

Specific cosmids which are useful in the practice of the present invention include:

PYGM, ZC7, XB11, 9.27, 6.6, 3.16, 23.20, NCAM, ZB6, CD3, THY1, 9.4, ETS1, 23.2, 5.8, LIF3E2II, and the like (see FIG. 3). Presently preferred cosmid probes include 23.2, which has the identifying sequence:

5'-ATACCCAACT-CACAGGATGC-TTCCTGGGAT-3' (SEQ. ID NO: 1), 5.8, which has the identifying sequence:

5'-AGCCTTCTTG-ACACCCTTGC-TGCTTTGGCC-3' (SEQ. ID NO: 2), and LIF3E2II, which has the identifying sequence:

5'-GTGAGTGCAG-GGATGGAAGT-ACTTG-3'(SEQ. ID NO: 3).

Cell samples to be analyzed by the invention technique can be employed directly without any particular preparation, or they can be subjected to conditions which promote growth, then arrested at metaphase [as described, for example, by Yunis and Chandler in *Clinical Diagnosis and Management by Laboratory Methods*, J. G. Henry, ed. (Saunders, Philadelphia) 16th Ed., pp 801–856 (1979)]. The latter procedure is presently preferred because it enables the visualization of the entire chromosome upon analysis, whereas the lack of cell preparation before hybridization generally allows visualization of only the sites of hybridization.

The presently preferred means of hybridization employed in the practice of the present invention is the technique of chromosomal in situ suppression hybridization (referred to hereinafter as "CISSH"), as recently described in *Science* 247:64–69 (1990). Similar techniques which can also be employed in the practice of the present invention have been described by Lawrence et al., in Cell 42: 51–61 (1988); Pinkel at al., in Proc. Natl. Acad. Sci. U.S.A. 83: 2934–2938 (1986); Pinkel et al., in Proc. Natl. Acad. Sci. U.S.A. 85: 9138–9142 (1988); and Trash et al., in Genomics 5: 710–717 (1989).

CISSH is carried out as follows:

20 to 50 ng of labeled probe DNA is combined with 1.5 to 3 μg of human placental DNA and sufficient salmon sperm DNA to obtain a total of 10 μl of hybridization cocktail. After denaturation of the probe mixture (75° C. for 5 min), preannealing of repetitive DNA sequences is allowed for 5 to 15 min (37° C.) before application to separately denatured chromosome specimens. Alternatively, in cases where no suppression and therefore no competitor DNA is needed, probe mixtures are denatured and then cooled on ice. When cosmid signals are obtained in parallel with a specific decoration of chromosome 11, 300 ng of pooled, labeled inserts from a chromosome 11 library is combined with the differentially labeled cosmid DNA probe. For delineation of human chromosome 11 the total DNA inserts of the library LA11NS02 derived from sorted chromosome 11 [M. A. VanDilla, et al., *Biotechnology* 4:537 (1986)] were prepared as described by Lichter, et al., *Human Genetics* 80:224 (1988). To obtain Alu banding simultaneously with the probe signal, the competitor DNA is substituted by 300 ng of differentially labeled pBS-Alu4, and preannealing is reduced to a few seconds. Alternatively, 100 ng of labeled pBS-Alu4 is denatured in hybridization cocktail, cooled on ice, and combined with a preannealed probe just before application to slides. After overnight incubation and posthybridization washes [see Lichter, et al., supra] the specimens are incubated with blocking solution [3% bovine serum albumin (BSA), 4×SSC (saline sodium citrate) or, when BSA cross-reacting DNP antibodies (anti-DNP) are used, 5% nonfat dry milk, 4×SSC] for 30 to 60 min at 37° C. For detection, all protein reagents are made up in 1% BSA, 4×SSC, and 0.1% Tween 20 (BSA cross-reacting antibodies are preincubated in this solution for 30 min. at 37° C.) and then incubated with the specimen (37° C., 30 min) and followed by washes (4×SSC, and 0.1% Tween 20, three times for 3 min. at 42° C.). Biotin-labeled probes detected by incubation with fluorescein isothiocyanate (FITC)-conjugated avidin (DCS grade; 5 μg/ml; available from Vector Laboratories, Burlingame, Calif.) or Texas Red™ isothiocyanate (TRITC)-conjugated ExtrAvidin (5 μg/ml) (Sigma). The signal of some short DNA probes (for example, pT24-Hras) is amplified as described by D. Pinkel et al., in *Proc. Natl. Acad. Sci. U.S.A.* 83:2934 (1986). DNP-labeled probes are detected by incubation with rabbit-anti-DNP (7 μg/ml) (Sigma) and a second incubation with FITC- or rhodamine-conjugated goat-anti-rabbit antibodies (8 μg/ml) (Boehringer Mannheim). Digoxigenin-labeled probes are incubated first with sheep-anti-digoxigenin Fab fragments (2.5 μg/ml) (Boehringer Mannhein) and then with FITC-conjugated donkey-anti-sheep antibodies (7 μg/ml) (Sigma). For single probe hybridizations, labeled DNA is detected by FITC-conjugates, and chromosomal DNA is counterstained by propidium iodide (PI) (200 ng/ml PI in 2×SSC, 5 min at room temperature). For hybridizations with multiple differentially labeled probes, chromosomal DNA is counterstained [see Lichter et al., supra] or banded [D. Schweizer, *Hum. Genet*, 57:1 (1981)] with diamidinophenylindole (DAPI). After mounting in antifading solution [see Lichter et al; Supra] the slides are evaluated on a Nikon Optiphot microscope equipped for conventional epifluorescence microscopy. For fine mapping, a modified version of the Bio-Rad laser scanning confocal microscope (Lasersharp MRC 500) is used in the photon counting mode (integration period of 0.1 to 0.3 ms per pixel) to produce digital images. The 488-nm line from an argon ion laser is used for excitation. In dual label experiments narrow band pass filters are used to obtain separate images of each fluorochrome (550-nm filter for FITC; 610-nm filter for PI or rhodamine). In some cases, the 532-nm line from an Amoco Microlaser [frequency-doubled diode-pumped Nd:YAG (yttrium-aluminum-garnet)] is used to excite rhodamine. The two separate images of one object are stored and then overlayed electronically. For image optimization, digital filtering is applied. Photographs can be taken from the video screen.

The invention will now be described in greater detail by reference to the following non-limiting examples.

EXAMPLES

Cell Lines

Human tumor cell lines TC71 and 6674 derived from Ewing's sarcoma, and TC32, derived from peripheral neuroepithelioma, were established at the National Institutes of Health, as described by Griffin, et al., in *Proc. Natl. Acad. Sci, U.S.A.* 83:6122–6126 (1986). All cell lines were shown to retain the previously described t(11q24;22q12) translocation by means of cytogenetic analysis and, as previously documented, demonstrated a wide variety of other numerical and/or structural chromosomal abnormalities. A human fibroblast cell line with a normal karyotype, CRL 1634, was obtained from the Human Genetic Mutant Cell Repository (Camden, N.J.) and used as a normal control.

Cosmid Clones

A set of over 1000 cosmid clones mapping to 11q13–11qter has been previously described by Evans, et al., (see *Proc. Nat'l Acad. Sci. U.S.A.* 86:5030–5034 (1989) and *Gene* 79:9–20 (1989); and a group of these cosmids were localized by CISSH. For this example, cosmids which map near the 11q24 Ewing's sarcoma translocation breakpoint were selected and used for in situ hybridization. Cosmids which contain the Thy-1 [see, for example, Wahl, et al., in Proc. Natl. Acad. Sci. U.S.A. 84: 2160–2164 (1987)], CD3 [see, for example, Evans, et al., in Immunogen. 28: 365–373 (1988)] and c-ets-1 [see, for example, Evans et al,.. in Proc. Natl. Acad. Sci. 86: 5030–5034 (1989) genes were identified using DNA or oligonucleotide or cDNA probes. Cosmid LIF3E2II carrying the human LIF gene, [described in *Nature* 336:690–692 (1988) and *Cancer Cells* 1:77–80 (1989)] was isolated from a human genomic cosmid library constructed in cosmid vector pWE15 [see Wahl, et al., in *Proc, Nat'l Acad. Sci. U.S.A.* 84:2160–2164 (1987)] using two synthetic 50 base oligonucleotides corresponding to bases 863–913 and 901–951 of the LIF gene coding region [see Gough et al., *Proc. Nat'l Acad. Sci, U.S,A,* 85: 2623–2627 (1988)]. Cosmid clone Hu-lambda 9, corresponding to the immunoglobulin lambda constant region gene mapping to human chromosome 22q11 [see Udey & Bloomberg in *Immunogen* 25:63–70 (1987)] was utilized to identify chromosome 22 in in situ hybridization experiments using mixed cosmid probes.

Cosmid DNA was prepared by cesium chloride density equilibrium centrifugation followed by treatment with ribonuclease A. Probes were labeled by primer extension using random oligomers in the presence of bio-11-dUTP (Enzo, New York, N.Y.) and bio-11-dCTP. The average size of the resulting probe, in the range of 200 to 300 bp, was obtained by pre-treating the cosmid DNA with deoxyribonuclease at 14° C. for 1 hour and the size distribution determined by alkaline agarose gel electrophoresis. Following labeling, the biotinylated cosmid probe was purified from unincorporated nucleotides by passage through Sephadex G-50 (Pharamacia) in a 1 ml spun microcolumn.

Slide Preparation and In Situ Suppression Hybridization (CISSH)

Metaphase chromosomes were prepared from actively growing cells by mitotic blockage and chromosomes spread on microscope slides using standard techniques [as described, for example, by Unis and Chandler in *Conical Diagnosis and Management by Laboratory Methods*, J. B. Henry, ed. (Saunders, Philadelphia) 16th Ed. pp 801–856 (1979)], with minor modifications. After synchronization of the cultures, Colcemid (0.1 µg/ml) was added for 30 to 60 min, and the cells treated with 0.075M potassium chloride (KCl) for 13 to 18 min followed by fixation in methanol/acetic acid. Precise hypotonic swelling and fixation conditions for optimal chromosome preparations were determined empirically for each cell type. Slides were stored at −20° C. before hybridization.

Interphase cells were harvested 5–6 days after complete confluency to obtain a relatively pure population of cells in the G1 phase. This was easily achieved with CRL1634 cells; while when using both ES and PNE cells, a population in G2 and M were present during the analysis. Cells were incubated for 15 minutes in 0,075M KCl, fixed in methanol and dropped on slides. Slides were prepared for hybridization by treatment with RNAse (100 µg/ml in 0.3M NaCl/30 mM sodium citrate (2X SSC) at 37° C. for 1 hr) followed by dehydration in 70%, 85% and 100% ethanol and by proteinase K digestion (0.5 µg/ml in 20 mM Tris/2 mM $CaCl_2$ at 37° C. for 7 min.) Slides were then fixed in 4% paraformaldehyde in phosphate-buffered saline plus 50 mM $MgCl_2$ at room temperature for 10 min. To denature chromosomes, slides were immersed in 70% formamide/2X SSC, pH 7.0, at 70° C. for 2 min and were then dehydrated in ice-cold 70%, 85% and 100% ethanol.

Hybridization and suppression reactions were carried out using modifications of previously described procedures. Briefly, 25–50 ng of biotinylated cosmid DNA was precipitated with 2 µg of human placental DNA, 1–2 µg of DNA from a plasmid containing a human Alu repetitive sequence pBLUR 8 [see Evans, et al., *Gene* 79:9–20 (1989)] and 7 µg of salmon sperm DNA. Competitor DNAs and salmon sperm DNA were treated with ribonuclease, extracted with phenol and chloroform, and sonicated to a final size range of 200–400 bp before use. Biotinylated cosmid DNA, coprecipitated with the competitor DNAs, was resuspended in 10 µl of hybridization buffer (50% formamide/2X SSC, pH 7.0, 10% dextran sulfate) and then denatured at 75° C. for 5 min. Preannealing was carried out for 15 min at 42° C. and hybridization reactions were carried out at 37° C. for 12–16 hr in a humidified chamber. Post-hybridization washes of the slides were carried out as previously described, with the last washing at 65° C. in 0.1X SSC.

The hybridization signal was visualized by treating the slides with flouresceinated avidin and biotinylated goat anti-avidin (Vector Laboratories, Burlingame, Calif.), both at 5 µg/ml, as previously described. The avidin and goat anti-avidin treatments were separated by three washes of 3 min each in 4X SSC, 4X SSC/0.1% Triton X and 0.1M phosphate buffer pH 8/0.1% Nonidet P-40, respectively. After the final avidin treatment, a fluorescence antifade solution containing 200 µg/ml of propidium iodide (PI) counterstain was applied under a coverslip.

Microscopy

Slides were initially evaluated using conventional epifluorescence. For fine structure analysis, images were produced using a laser scanning confocal microscope (BioRad MRC 500) and narrow band pass filters were used to obtain separate images for FITC (550 nm) and propidium iodide (610 nm) which were then superimposed electronically.

Pulsed Field Gel Electrophoresis (PFGE)

DNA was obtained from the fibroblast cell lines CRL 1634, TC32, TC71 and 6674 in agarose plugs as previously described by Selleri et al., in *Blood* 75:1146–1153 (1990). The DNA was digested with several different rare-cutting enzymes including NotI, BssHII, SfiI and MluI, and analyzed using the HEX-CHEF system (CBS Scientific, Del Mar, Calif.) at 180 V/cm for 24 hours using program B. DNA was transferred to nylon hybridization membranes and hybridized to DNA probes labeled with $^{32}$P-dCTP by random oligomer priming. *S. cerevisiae* chromosomes were utilized as size markers.

Results

To identify the precise location of the 11;22 translocation associated with ES and PNE, a set of ordered cosmid DNA markers previously mapped on chromosome 11q by CISHH was utilized. These ordered cosmid clones were labeled and sequentially hybridized to metaphase chromosomes from normal, ES or PNE cell lines and the location of the hybridization signal on the normal and derivative chromosome 11 or 22 determined. In the absence of traditional cytogenetic "banding", chromosomes were identified by hybridization with additional cosmid clone Hu-lambda 9 containing the human immunoglobulin lambda constant region gene on chromosome 22, or cosmid previously mapped to chromosome 11. Hybridization to both sister chromatids of the normal or derivative chromosomes was seen in 85–90% of metaphases examined; through electronic enlargement using a confocal laser scanning microscope, the fractional chromosomal length (FLpter) was determined on normal DNA derivative chromosomes. Consistent with previous reports [see, for example, Griffin et al., *Proc. Nat'l Acad. Sci. U.S.A.* 83: 6122–6126 (1986)], cosmids containing the c-ets-1, Thy-1, and CD3 genes were located centromeric to the translocation breakpoint. Additional cosmid clones were separated based on the centromeric or telemetric position relative to the breakpoint. Two cosmid clones were identified which immediately flank the ES breakpoint shown in FIG. 3. Cosmid clone 23.2, previously mapped at FLpter 0.98, was present on the derivative chromosome at FLpter 0.88, a consequence of significant elongation of the chromosome due to the translocated fragment of chromosome 22 (FIG. 3). Cosmid clone 5.8, previously mapped with an FLpter of 0.98, was found to be translocated to the derivative chromosome 22 in both ES and PNE metaphases (FIG. 3).

Since clones 23.2 and 5.8 were previously shown to be separated by less than 1% of the chromosome length (less than approximately 1.5 mb) by measurements of distance from the 11p telomere, a more precise determination of the physical separation of these two clones was carried out by pairwise hybridization of cosmids. Cones 23.2 and 5.8 were labeled and simultaneously hybridized to normal, ES and PNE metaphase chromosomes demonstrating four fluorescent spots on the normal chromosome 11 in 70% of metaphases examined. Two fluorescent spots were observed on each of the derivative chromosomes 11 and 22 respectively, demonstrating that the translocation separates these two closely spaced markers. This analysis demonstrates that this separation corresponds to a physical distance between these two indicators of roughly 1 mb.

Previous analysis by Sutherland et al. [see *Leukemia* 3:9–13 (1989)] established that the gene encoding LIF, an interleukin involved in the regulation of cell growth, mapped to chromosome 22q12 in the cytogenetic vicinity of the ES translocation breakpoint. To determine if the translocation occurred near this gene, the relationship of the LIF gene to the ES breakpoint was determined by isolating a series of cosmid clones containing the LIF gene from a human genomic cosmid library using synthetic probes based on published sequences. To determine the precise chromosomal location relative to other cosmid markers, CISSH was carried out using metaphase chromosomes from normal human, ES and PNE cells. The LIF gene mapped to the normal chromosome 22 with an FLpter of 0.60, corresponding to the band 22q12. When the LIF cosmid was used in hybridization to metaphases from ES cell lines TC71 and 6647, two hybridization signals were found on the normal chromosome 22 and hybridization signals were observed on the derivative chromosome 11 at FLpter 0.92. Thus, the LIF gene is seen to be located distal to the t(11;22) translocation breakpoint on chromosome 22 and is relocated onto the derivative chromosome 11 as a consequence of this chromosomal rearrangement. Identical hybridization positions were observed on metaphases from the PNE cell line TC32, suggesting that the ES and PNE translocations are in the same relative location. To determine the location and distance of the translocated LIF gene to the cosmids flanking the chromosome 11 breakpoint, simultaneous CISSH analysis using the LIF cosmid and clone 23.3 was carried out using ES and PNE cell lines, demonstrating four florescent spots located at FLpter 0.88–0.92, two on each chromatid, on the derivative chromosome 11. Metaphase and interphase analysis of distance using the same size standard as described above, suggested that the LIF-23.2 distance on the derivative chromosome was less than 1 mb.

Since the LIF gene encodes an interleukin with significant developmental effects on cell growth, it is conceivable that the ES translocation interrupts or activates the LIF gene and is responsible for the etiology of the malignancy. To investigate whether the LIF gene would be interrupted by the translocation, thus altering its expression, pulsed field gel analysis was carried out to probe the region of chromosome 22 in the vicinity of the LIF gene for evidence of rearrangements. DNA from the normal fibroblast cell line and normal peripheral blood lymphocytes, as well as DNA isolated from ES and PNE cell lines, were digested with different rare-cutting restriction enzymes (MluI, BssHII, SfiI, NotI) and hybridized to a repeat free probe prepared from cosmid LIF3E2II. Unique fragments were identified in normal, ES and PNE DNA samples and no evidence of rearrangements occurring within these fragments was observed. Since cosmid LIF3E2II (from which the repeat free probe was generated) did not contain internal NotI or BsshII sites, this data indicates that the t(11;22) translocation breakpoint in both ES and PNE cell lines lies outside a 650 kb genomic fragment spanning the LIF gene. Given the separation of LIF and clone 23.2 on the derivative chromosome of less than 1 mb, this limits the area of the breakpoint to a small genomic region.

The invention has been described in detail with particular reference to preferred embodiments thereof, but it will be understood that variations and modifications can be effected within the spirit and scope of the invention.

---

That which is claimed is:

1. A method for distinguishing a neuroepithelial tumor associated with chromosome 11,22 translocations from other tumors, said method comprising:
   (a) hybridizing intact chromosomal DNA from a subject with at least one clone specific for chromosome 11 and/or chromosome 22 which is diagnostic for the existence of a neuroepithelial-tumor-associated chromosome 11,22 translocation, and
   (b) identifying intact chromosomal DNA which has a different pattern of hybridization, relative to the pattern of hybridization of said clone when hybridized with intact chromosomal DNA free of any aberrations, as being indicative of the presence of, or susceptibility to, a neuroepithelial tumor associated with a chromosome 11,22 translocation, wherein said at least one clone is clones 23.2, 5.8, LIF3E2II, or a clone specific for chromosome 11 that hybridizes to chromosome 11 at a point distal to clone 23.2 and proximal to clone 5.8.

2. A method according to claim 1 wherein said neuroepithelial tumor is selected from the group consisting of: Ewing's Sarcoma, peripheral neuroepithelioma, and Askin's tumor.

3. A method according to claim 1 wherein the presence of the neuroepithelial tumor, Ewing's sarcoma, is distinguished from the presence of other bone tumors.

4. A method according to claim 1 wherein the presence of the neuroepithelial tumor, peripheral neuroepithelioma, is distinguished from the presence of other tumors.

5. A method according to claim 1 wherein the presence of the neuroepithelial tumor, Askin's tumor, is distinguished from the presence of other chest wall tumors.

6. A method according to claim 1 wherein said at least one clone specific for chromosome 22 is clone LIF3E2II.

7. A method for distinguishing a neuroepithelial tumor associated with chromosome 11,22 translocations from other tumors, said method comprising:
   (a) hybridizing intact chromosomal DNA from a subject with a at least one clone specific for chromosome 11 and/or chromosome 22 which is diagnostic for the existence of a neuroepithelial-tumor-associated chromosome 11,22 translocation, and
   (b) identifying intact chromosomal DNA which has a different pattern of hybridization, relative to the pattern of hybridization of said at least one clone when hybridized with intact chromosomal DNA free of any aberrations, as being indicative of the presence of, or susceptibility to, a neuroepithelial tumor associated with a chromosome 11,22 translocation, wherein said at least one clone specific for chromosome 11, and/or chromosome 22 is a combination of clones selected from the group consisting of: 23.2 and LIF3E2II; and 5.8 and LIF3E2II.

8. A method for screening for a neuroepithelial tumor associated chromosome 11,22 translocation in a mammalian subject comprising:
   (a) contacting intact chromosomal DNA from said subject with at least one clone specific for chromosome 11 and/or chromosome 22 which is diagnostic for the existence of neuroepithelial tumor cell growth associated with a chromosome 11,22 translocation, and
   (b) identifying intact chromosomal DNA which has a different pattern of hybridization, relative to the pattern of hybridization of said clone when hybridized with intact chromosomal DNA free of any aberrations, as being indicative of the presence of, or susceptibility to, a neuroepithelial tumor associated with a chromosome 11,22 translocation, wherein said at least one clone is clones 23.2, 5.8, LIF3E2II, or a clone specific for chromosome 11 that hybridizes to chromosome 11 at a point distal to clone 23.2 and proximal to clone 5.8.

9. A method according to claim 8 wherein said neuroepithelial tumor is selected from the group consisting of: Ewing's Sarcoma, peripheral neuroepithelioma, and Askin's tumor.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 30 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

ATACCCAACT CACAGGATGC TTCCTGGGAT 30

( 2 ) INFORMATION FOR SEQ ID NO:2:

( i ) SEQUENCE CHARACTERISTICS:
      ( A ) LENGTH: 30 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:2:

AGCCTTCTTG ACACCCTTGC TGCTTTGGCC 30

( 2 ) INFORMATION FOR SEQ ID NO:3:

( i ) SEQUENCE CHARACTERISTICS:
      ( A ) LENGTH: 25 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:3:

GTGAGTGCAG GGATGGAAGT ACTTG 25